United States Patent
Lu et al.

(10) Patent No.: US 9,126,901 B2
(45) Date of Patent: Sep. 8, 2015

(54) PROCESS FOR THE PREPARATION OF AMINONITRILE AND DIAMINE, AND CORRESPONDING DEVICES

(75) Inventors: Zhongjie Lu, Jiangsu (CN); Shiquan Diao, Jiangsu (CN); Xinjun Zhang, Jiangsu (CN); Peijun Xu, Jiangsu (CN)

(73) Assignees: SOLVAY (ZHANGJIAGANG) SPECIALTY, Jiangsu (CN); CHEMICALS CO., LTD.; RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 14/127,526

(22) PCT Filed: Jul. 7, 2011

(86) PCT No.: PCT/CN2011/076933
§ 371 (c)(1),
(2), (4) Date: Jan. 21, 2014

(87) PCT Pub. No.: WO2013/004016
PCT Pub. Date: Jan. 10, 2013

(65) Prior Publication Data
US 2014/0194643 A1    Jul. 10, 2014

(51) Int. Cl.
*C07C 209/48* (2006.01)
*C07C 253/30* (2006.01)

(52) U.S. Cl.
CPC ............. *C07C 253/30* (2013.01); *C07C 209/48* (2013.01)

(58) Field of Classification Search
CPC ....... C07C 209/48; C07C 253/30; B01J 8/025
USPC .................................................. 558/454, 457
See application file for complete search history.

(56) References Cited

U.S. PATENT DOCUMENTS

| 4,375,003 A | 2/1983 | Allain et al. |
| 4,739,120 A | 4/1988 | Zuckerman |
| 5,869,653 A | 2/1999 | Johnson |
| 6,518,449 B1 | 2/2003 | Boschat et al. |

FOREIGN PATENT DOCUMENTS

CN    101443306 A    5/2009

*Primary Examiner* — Nyeemah A Grazier
(74) *Attorney, Agent, or Firm* — Xuping Fu

(57) ABSTRACT

The present invention relates to a continuous process for the preparation of an aminonitrile comprising the stages of:
a) formation of the aminonitrile by reaction between an alkenyl nitrile, mixed with aminonitrile, and a monoamine introduced in molar excess with respect to the alkenyl nitrile;
b) separation of the unreacted monoamine and the aminonitrile;
c) reaction between the monoamine separated during stage b) and all or part of the alkenyl nitrile in order to form a mixture of aminonitrile and of unreacted alkenyl nitrile, with the alkenyl nitrile being introduced in molar excess with respect to the said monoamine;
d) transfer of the mixture of aminonitrile and alkenyl nitrile resulting from stage c) to the reaction of stage a), and
e) in the case where only a portion of the alkenyl nitrile is introduced during stage c), introduction of the remaining molar amount of alkenyl nitrile into the mixture of stage d).

14 Claims, 1 Drawing Sheet

PROCESS FOR THE PREPARATION OF AMINONITRILE AND DIAMINE, AND CORRESPONDING DEVICES

CROSS-REFERENCE TO RELATED APPLICATIONS

This application is a U.S. national stage entry under 35 U.S.C. §371 of International Application No. PCT/CN2011/076933 filed Jul. 7, 2011, the whole content of this application being herein incorporated by reference for all purposes.

TECHNICAL FIELD

The present invention relates to a continuous process for the preparation of aminonitrile, in particular 3-(dimethylamino)propanenitrile (DMAPN), by reaction between the corresponding monoamine, in particular dimethylamine (DMA) and the corresponding alkenyl nitrile, in particular acrylonitrile (AN). The invention also relates to the device of use in the implementation of this process.

The present invention also relates to a process for the preparation of diamine, in particular N,N-dimethyl-1,3-propanediamine (DMAPA) comprising the continuous preparation of aminonitrile. The invention also relates to the device of use in the implementation of this process.

BACKGROUND ART

A process for the preparation of DMAPN by reaction between AN and DMA is already known. Generally, DMA and AN are introduced into the reactor in the stoichiometric amount or with an excess of DMA.

However, the disadvantage of the stoichiometric introduction is that the yield is not sufficient. DMA has a very low boiling point (of the order of 7° C.); thus, when it is introduced in excess, if it is desired to recycle the unreacted DMA, a distillation has to be carried out and also a condensation of the DMA vapours obtained, which substantially increases the investments and increases the manufacturing costs.

It is therefore necessary to provide a process for the preparation of aminonitrile which provides a solution to all or some of the problems of the processes of the state of the art, in particular on the industrial scale.

SUMMARY OF THE INVENTION

One object of the present invention is to provide a process for the preparation of aminonitrile, in particular DMAPN, with an enhanced yield and enhanced kinetics with respect to the processes of the prior art, which makes possible simple and relatively inexpensive recycling of the reactant introduced in excess.

One object of the invention is also to provide a process which is advantageous from an industrial viewpoint.

Another object of the invention is to provide a process for the preparation of diamine, in particular N,N-dimethyl-1,3-propanediamine (DMAPA), comprising the preparation of aminonitrile, in particular of DMAPN, with an enhanced yield and enhanced kinetics with respect to the processes of the state of the art, which makes possible simple and relatively inexpensive recycling of the reactant introduced in excess.

The present invention relates to a continuous process for the preparation of an aminonitrile comprising the stages of:
a) formation of the aminonitrile by reaction between an alkenyl nitrile, mixed with aminonitrile, and a monoamine introduced in molar excess with respect to the alkenyl nitrile;
b) separation of the unreacted monoamine and the aminonitrile;
c) reaction between the monoamine separated during stage b) and all or part of the alkenyl nitrile in order to form a mixture of aminonitrile and of unreacted alkenyl nitrile, with the alkenyl nitrile being introduced in molar excess with respect to the said monoamine;
d) transfer of the mixture of aminonitrile and alkenyl nitrile resulting from stage c) to the reaction of stage a),
e) in the case where only a portion of the alkenyl nitrile is introduced during stage c), introduction of the remaining molar amount of alkenyl nitrile into the mixture of stage d);
the total molar amount of alkenyl nitrile introduced during stages c) and e) being equal to the molar amount of monoamine introduced during stage a).

It should be understood that the reaction of stage c) is not carried out in the same reactor as that of stage a).

DETAILED DESCRIPTION OF THE INVENTION

Figure 1:
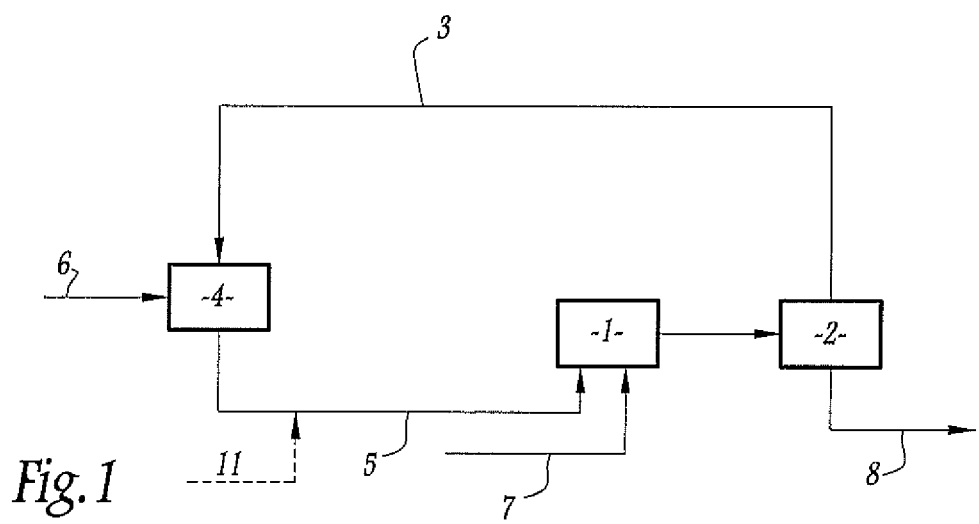
FIG. 1 represents an exemplary device for preparation of an aminonitrile according to the invention.

The alkenyl nitrile comprises at least one carbon-carbon double bond. It is preferably chosen from linear or branched $C_2$ to $C_4$ alkenes in which a hydrogen atom is replaced by a conjugated cyano group, that is to say that the alkenyl nitrile comprises a double bond in the $\alpha,\beta$ position with respect to the cyano group. Examples of $C_2$ to $C_4$ alkene are in particular ethene, propene, 1-butene, 2-butene, 2-methylpropene. Examples of alkenyl nitriles are, for example, acrylonitrile, 2-butenenitrile, methacrylonitrile, 2-pentenenitrile, 2-ethylacrylonitrile, 2-methyl-2-butenenitrile and 3-methyl-2-butenenitrile.

Preferably, the alkenyl nitrile is acrylonitrile (AN).

The monoamine is preferably a secondary amine of general formula $R^1R^2NH$, in which $R^1$ and $R^2$, which are identical or different, represent a linear or branched $C_1$ to $C_4$ alkyl. Mention may be made, as examples of $C_1$ to $C_4$ alkyl, of methyl, ethyl, n-propyl, isopropyl, 1-n-butyl, 2-n-butyl, isobutyl or t-butyl.

Preferably, the monoamine is dimethylamine (DMA).

Preferably, the aminonitrile is 3-(dimethylamino)propanenitrile (DMAPN) resulting from the addition of dimethylamine (DMA) to acrylonitrile (AN).

The total amount of monoamine introduced during stages a) and c) is in molar excess, for example in an excess of at least 0.1 mol %, for example of between 1 and 50 mol %, for example of between 5 and 35 mol %, with respect to the total amount of alkenyl nitrile employed in the process of the invention.

During stage b) of the process of the invention, the separation of the monoamine and the aminonitrile can be carried out in particular by distillation and/or flash distillation.

The stage of distillation and/or of flash distillation, can be carried out at atmospheric pressure or at reduced pressure, in particular at a pressure of less than 0.9 bar, for example at a pressure of between 0.1 and 0.8 bar.

During the implementation of stage c) of the process of the invention, the alkenyl nitrile is present in excess, in particular in an excess of at least 1 mol %, with respect to the monoamine, for example of at least 5 mol %, with respect to the monoamine.

In one embodiment, all the alkenyl nitrile is introduced in stage c).

In another embodiment, a portion of the alkenyl nitrile is introduced in stage c), the remainder being introduced in stage d).

Preferably, the temperature during stages a) and c) is independently between 25 and 110° C. The pressure during stages a) and c) is adjusted so that the monoamine is maintained in a liquid phase. For example, the pressure during stages a) and c) can be independently between 1 and 15 bar.

The invention also relates to a process for the preparation of a diamine, comprising the stages of:
(i) continuous preparation of an aminonitrile according to the invention;
(ii) reduction of the aminonitrile in order to form the diamine.

Preferably, the aminonitrile is DMAPN and the diamine is DMAPA.

The reduction of stage (ii) can be carried out by any method known to a person skilled in the art, for example by hydrogenation. Such hydrogenation processes are described in particular in Patent Applications or U.S. Pat. No. 5,869,653, U.S. Pat. No. 6,518,449, U.S. Pat. No. 4,375,003 and U.S. Pat. No. 4,739,120.

The process for the preparation of a diamine can also comprise a stage of purification of the diamine obtained. This purification stage can be carried out by any method known to a person skilled in the art, in particular by distillation at atmospheric pressure or under reduced pressure.

The present invention also relates to a device for the preparation of an aminonitrile by reaction between a monoamine and an alkenyl nitrile. An example of such a device according to the invention is represented in FIG. 1.

This device of use in the preparation of an aminonitrile comprises:
a reactor (1) for the reaction between an alkenyl nitrile, mixed with the aminonitrile, and a monoamine in molar excess with respect to the alkenyl nitrile, in order to form the aminonitrile;
a separation device (2) which makes possible the separation of the unreacted monoamine and the aminonitrile;
a device (3) for conveying the monoamine separated by means of the device (2) to a reactor (4);
a reactor (4) for the reaction between the monoamine separated by means of the device (2) and all or a portion of the alkenyl nitrile, in molar excess with respect to the monoamine, in order to form a mixture of aminonitrile and unreacted alkenyl nitrile;
a device (5) for conveying the mixture of aminonitrile and alkenyl nitrile exiting from the reactor (4) to the reactor (1).

According to the invention, the conveying device is any device known to a person skilled in the art which makes possible the transfer of a fluid from one apparatus to another, for example a pump.

The separation device (2) is in particular a distillation device or a flash distillation device, or a combination of these devices.

The device according to the invention also comprises a means (6) for introduction of the alkenyl nitrile into the reactor (4) and a means (7) for introduction of the monoamine into the reactor (1). The device also comprises a means (8) for recovery of the aminonitrile formed.

Optionally, the device according to the invention can additionally comprise a means (11) for the introduction of alkenyl nitrile into the conveying device (5).

Such an introduction means (11) can in particular be added to the device of the invention in the case where only a portion of the alkenyl nitrile is introduced into the reactor (4), it being understood that the total molar amount of alkenyl nitrile introduced into the reactor (4) and via the introduction means (11) has to be equal to the molar amount of monoamine introduced into the reactor (1).

The introduction and recovery means can be any means known to a person skilled in the art.

Figure 2:
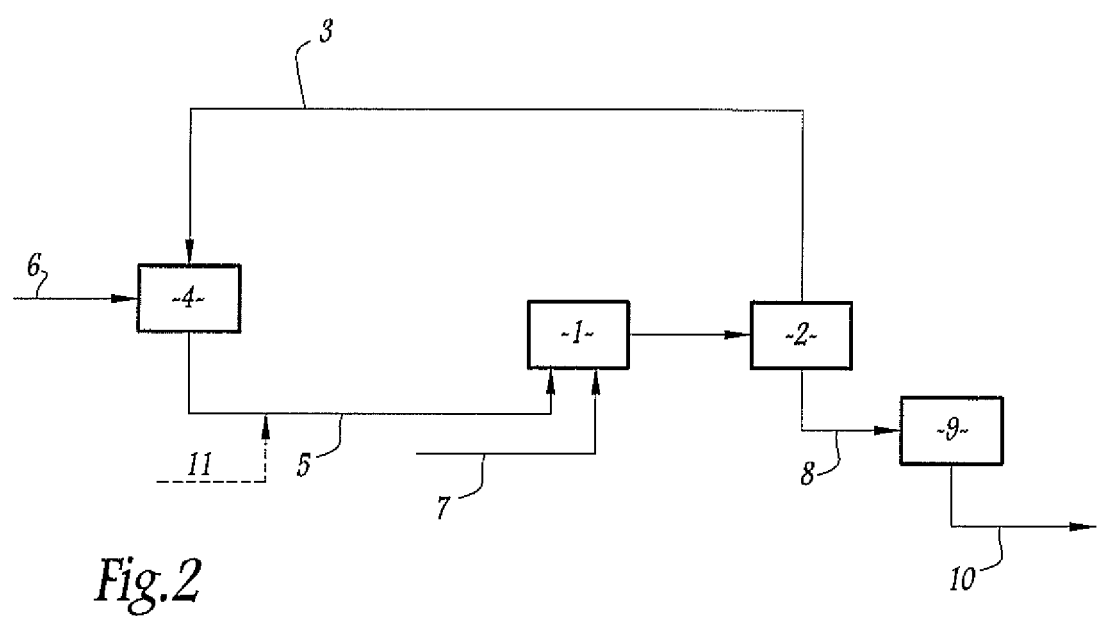
FIG. 2 represents an exemplary device for preparation of an diamine according to the invention.

The invention also relates to a device for the preparation of a diamine from an aminonitrile. An example of such a device according to the invention is represented in FIG. 2.

This device, of use in the preparation of a diamine, is identical to the device described above for the preparation of an aminonitrile and additionally comprises a device (8) for conveying the aminonitrile separated by means of the device (2) to a reactor (9) in order to be subjected to a reduction reaction in order to form the diamine. The means for introducing the hydrogen necessary for the reduction reaction are not represented in FIG. 2.

The device for the preparation of the diamine also comprises a means (10) for recovery of the diamine formed and can optionally comprise a means for purification of the diamine obtained, for example one or more distillation columns.

Example

Synthesis of DMAPN 553 g/h of AN and 138 g/h of gaseous DMA per liter of reactor are continuously introduced into a stirred reactor maintained at a temperature of 50° C. The residence time in this reactor is of the order of 1.2 h.

At the outlet of this stirred reactor, 469 g/h of DMA are mixed using a static mixer in order to feed a tubular reactor maintained at 65° C. under a pressure of 5 bar. The residence time in this reactor is of the order of 10 min.

The reaction mixture exiting from the reactor feeds a distillation column under 0.5 bar. The DMA exiting at the column top is cooled to 50° C. and recycled to the stirred reactor.

The DMAPN produced at the column bottom comprises less than 0.06% of AN.

The invention claimed is:
1. A continuous process for the preparation of an aminonitrile comprising the stages of:
a) formation of an aminonitrile by reaction between an alkenyl nitrile, mixed with aminonitrile, and a monoamine introduced in molar excess with respect to the alkenyl nitrile;
b) separation of the unreacted monoamine and the aminonitrile;
c) reaction between the monoamine separated during said stage b) and all or part of the alkenyl nitrile in order to form a mixture of aminonitrile and of unreacted alkenyl nitrile, with the alkenyl nitrile being introduced in molar excess with respect to the said monoamine;
d) transfer of the mixture of aminonitrile and alkenyl nitrile resulting from said stage c) to the reaction of stage a), and
e) in the case where only a portion of the alkenyl nitrile is introduced during stage c), introduction of the remaining molar amount of alkenyl nitrile into the mixture of said stage d);

the total molar amount of the alkenyl nitrile introduced during said stages c) and e) being equal to the molar amount of monoamine introduced during said stage a).

2. The process according to claim 1, wherein the alkenyl nitrile is selected from the group consisting of linear and branched C2 to C4 alkenes wherein a hydrogen atom is replaced by a conjugated cyano group.

3. The process according to claim 1, wherein the monoamine is a secondary amine of general formula R1R2NH, wherein R1 and R2, which are identical or different, represent a linear or branched C1 to C4 alkyl.

4. The process according to claim 1, wherein:
the alkenyl nitrile is acrylonitrile (AN);
the monoamine is dimethylamine (DMA); and
the aminonitrile is 3-(dimethylamino)propanenitrile (DMAPN).

5. The process according to claim 1, wherein the total amount of monoamine introduced during said stages a) and c) is in molar excess with respect to the total amount of alkenyl nitrile.

6. The process according to claim 1, wherein the separation of said stage b) is carried out by distillation and/or flash distillation.

7. The process according to claim 1, wherein the separation of said stage b) is carried out at atmospheric pressure.

8. The process according to claim 1, wherein the separation of said stage b) is carried out under reduced pressure.

9. The process according to claim 8, wherein the pressure is less than 0.9 bar.

10. The process according to claim 8, wherein the pressure is between 0.1 and 0.8 bar.

11. The process according to claim 1, wherein, during said stage c), the alkenyl nitrile is introduced in an excess of at least 1 mol % with respect to the monoamine.

12. The process for the preparation of a diamine, comprising the stages of:
(i) continuous preparation of an aminonitrile according to the process of claim 1; and
ii) reduction of the aminonitrile resulting from stage (i).

13. The process according to claim 12, wherein the diamine is dimethylaminopropylamine (DMAPA).

14. The process according to claim 1 wherein the total amount of monoamine introduced during said stages a) and c) is in an excess of at least 0.1 mol %, with respect to the total amount of alkenyl nitrile.

* * * * *